United States Patent [19]

Holtkamp

[11] Patent Number: Plant 5,489

[45] Date of Patent: Jun. 11, 1985

[54] AFRICAN VIOLET PLANT NAMED CLEVELAND

[75] Inventor: Reinhold Holtkamp, Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 535,396

[22] Filed: Sep. 23, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet plant named Cleveland characterized by its intensive purple-red flower color which is resistant to fading under high temperatures, its girl type leaves, which are medium to dark green and shiny, with bright green leaf centers, strong and upright flower stems, and by its vigorous yet compact growth habit.

1 Drawing Figure

The present invention comprises a new and distinct cultivar of African violet plant, botanically known as *Saintpaulia ionantha,* and named Cleveland.

The new cultivar was referred to during the breeding and selection process by the designation F 27/1, and is a product of a planned breeding program. The basic objective of the breeding program was to create a new African violet cultivar having red-purple flower color and "girl" type leaves, that is, leaves that are generally concave when viewed from above, and possessing two-toned green color, with the light green appearing in the center of the leaf.

The new cultivar was originated from a cross made in a controlled breeding program in Isselburg, West Germany. The female, or seed plant was a cultivar designated D 150/2 red girl. The male, or pollen parent was a cultivar named Delaware, disclosed in U.S. Plant Pat. No. 4,213.

The new cultivar Cleveland was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Cleveland has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn., under greenhouse conditions which closely approximate those generally used in commercial practice.

The following traits have been repeatedly observed and are determined to be basic characteristics of Cleveland, which in combination distinguish this African violet as a new and distinct cultivar:

1. Intensive purple-red flower color which does not fade under high temperatures and which provides a very attractive contrast with the foliage color.

2. Girl type leaves which are shiny and medium to dark green except for a bright green leaf center.

3. Vigorous growth habit when compared to other girl type varieties; despite the vigorous growth, the compact structure of the plant is maintained.

4. The flowers are carried on stems which are strong, sturdy and upright, with seven and more flower stems carrying up to 4–7 flowers per stem.

5. The flowers are long lasting and non-dropping.

6. Due to its compact growth habit, individual plants can be grown relatively close together without stretching the petioles.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 2:00 P.M. in early September in Nashville, Tenn.

Botanical classification: *Saintpaulia ionantha,* Ramat. cv. Cleveland.

Parentage:

*Male parent.*—Delaware, disclosed in U.S. Plant Pat. No. 4,213.

*Female parent.*—D 150/2 red girl.

Propagation: The new cultivar holds its distinguishing characteristics through successive propagations by leaf cuttings and by division of shoots.

Plant: From 6 cm. to 8 cm. tall when grown in pots, and approximately 20 cm. in diameter when fully grown.

*Leaves.*—General form: Heart shaped to round. Diameter: 60 mm. Texture: Leather-like. Aspect: Velvety, slightly hairy. Veins: Pronounced, light green and shiny. Color (upperside): Green 137A-B. Color (underside): Yellow Green 147D. Petiole: Brownish green; hairy.

*Flowers.*—Buds: Bell shaped, deep purplish red. Sepals: Dark brown; 5 in number. Color: Red purple 74A-B. Calyx: Funnel shaped. Aspect: Spear shaped; hairy. Peduncle: Short upright; sturdy; brownish green.

*Individual flowers.*—Size: 40–45 mm. Color: Upperside: Red purple 74, between A and B. Underside: Purple 78B. Borne: On sturdy and upright flower stems, each carrying 7 or more flowers on short strong peduncles. Shape: Conventional violet shaped, two small and three large petals; single flower. Flowering time: 9–10 weeks after potting to saleable, decorative plant.

*Reproductive organs.*—Anthers: Two, composed of four anther cells; seed capsule pushed slightly through. Filaments: Light green. Styles: 5 mm; long, glassy tip.

*Roots.*—White when young and active, green brown when older, normally developed.

*Disease resistance.*—Good as experienced to date.

General observations: Cleveland is a vigorous grower when compared with other girl type African violet varieties, while maintaining a compact structure. This permits individual plants to be grown relatively close to each other without stretching the petioles. The leaves are medium to dark green with bright green leaf centers typical of girl leaves, with the leaves pleasantly contrasting with the intensive purple-red flower color. The flowers are carried on strong and upright flower stems, and the flowers are resistant to fading under high temperatures and non-dropping.

I claim:

1. An African violet plant named Cleveland, as described and illustrated, and particularly characterized by its intensive purple-red flower color which is resistant to fading under high temperatures, its girl type leaves, which are medium to dark green and shiny, with bright green leaf centers, strong and upright flower stems, and by its vigorous yet compact growth habit.

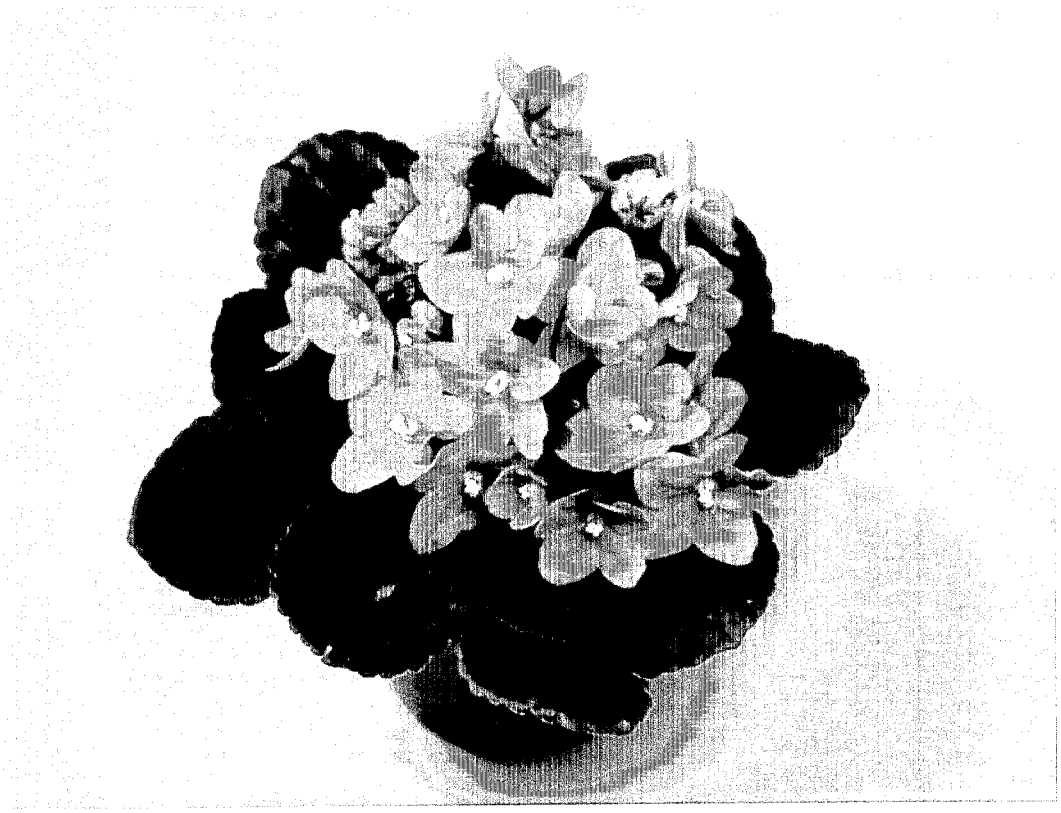

* * * * *